(12) United States Patent
Li et al.

(10) Patent No.: US 7,291,129 B2
(45) Date of Patent: Nov. 6, 2007

(54) APPARATUS AND METHODS FOR TREATING FEMALE URINARY INCONTINENCE

(75) Inventors: Hong Li, San Diego, CA (US); Peter S Edelstein, Menlo Park, CA (US); John T To, Newark, CA (US); Simon W. H. Thomas, Danville, CA (US); Benjamin T Nordell, San Mateo, CA (US)

(73) Assignee: Novasys Medical Inc., Newark, CA (US)

( * ) Notice: Subject to any disclaimer, the term of this patent is extended or adjusted under 35 U.S.C. 154(b) by 801 days.

(21) Appl. No.: 10/207,689

(22) Filed: Jul. 25, 2002

(65) Prior Publication Data

US 2003/0036804 A1    Feb. 20, 2003

Related U.S. Application Data

(63) Continuation-in-part of application No. 09/678,500, filed on Oct. 2, 2000, now Pat. No. 6,470,219.

(51) Int. Cl.
*A61M 5/178* (2006.01)

(52) U.S. Cl. .............................. 604/164.01; 604/164.09

(58) Field of Classification Search ................ 604/500, 604/506–509, 93.01, 96.01, 102.01, 104–109, 604/158–159
See application file for complete search history.

(56) References Cited

U.S. PATENT DOCUMENTS

| 5,366,490 | A |  | 11/1994 | Edwards et al. |
| 5,454,782 | A |  | 10/1995 | Perkins |
| 5,458,596 | A |  | 10/1995 | Lax et al. |
| 5,464,395 | A |  | 11/1995 | Faxon et al. |
| 5,536,240 | A | * | 7/1996 | Edwards et al. ............... 604/22 |
| 5,569,241 | A |  | 10/1996 | Edwards |
| 5,588,960 | A |  | 12/1996 | Edwards et al. |
| 5,785,642 | A |  | 7/1998 | Wallace et al. |
| 5,813,411 | A |  | 9/1998 | Van Bladel et al. |
| 5,868,708 | A |  | 2/1999 | Hart et al. |
| 5,957,920 | A |  | 9/1999 | Baker |
| 5,964,755 | A |  | 10/1999 | Edwards |
| 6,044,846 | A |  | 4/2000 | Edwards |
| 6,071,230 | A |  | 6/2000 | Henalla et al. |
| 6,077,257 | A |  | 6/2000 | Edwards et al. |
| 6,091,995 | A |  | 7/2000 | Ingle et al. |
| 6,254,586 | B1 |  | 7/2001 | Mann et al. |
| 6,254,598 | B1 |  | 7/2001 | Edwards et al. |
| 6,425,854 | B1 |  | 7/2002 | Galt et al. |
| 6,463,331 | B1 |  | 10/2002 | Edwards et al. |
| 6,470,219 | B1 |  | 10/2002 | Edwards et al. |
| 6,478,775 | B1 |  | 11/2002 | Galt et al. |
| 6,666,848 | B2 | * | 12/2003 | Stone .................... 604/164.01 |

* cited by examiner

*Primary Examiner*—Catherine S. Williams
(74) *Attorney, Agent, or Firm*—Jones Day; Nicole A. Pisano

(57) ABSTRACT

Apparatus and methods are provided for treating female urinary incontinence by injecting a bulking agent at the interface between the mucosal and submucosal layers of the urethral wall. The remodeling device comprises an elongated shaft preferably having means for forming a localized inward protrusion of the urethral wall, and a needle, movable between retracted and deployed positions, for delivering a bulking agent into the urethral wall in the vicinity of the localized inward protrusion to thereby reduce or eliminate symptoms associated with urinary incontinence.

16 Claims, 5 Drawing Sheets

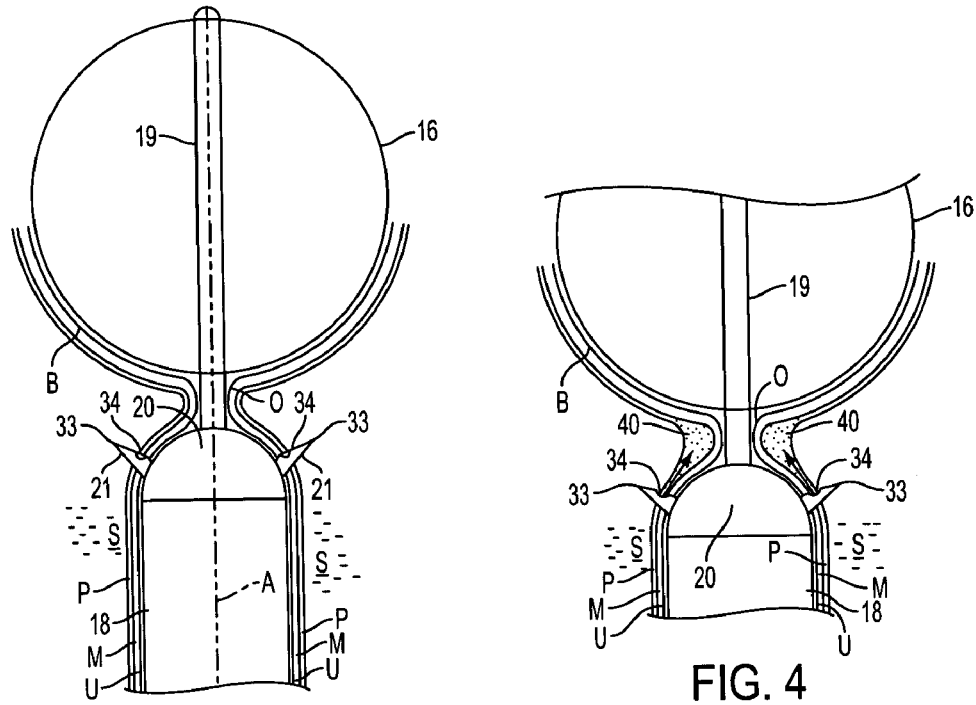
FIG. 3
FIG. 4
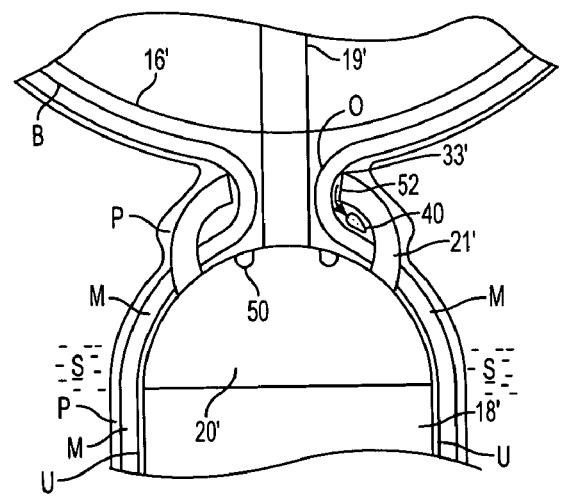
FIG. 5

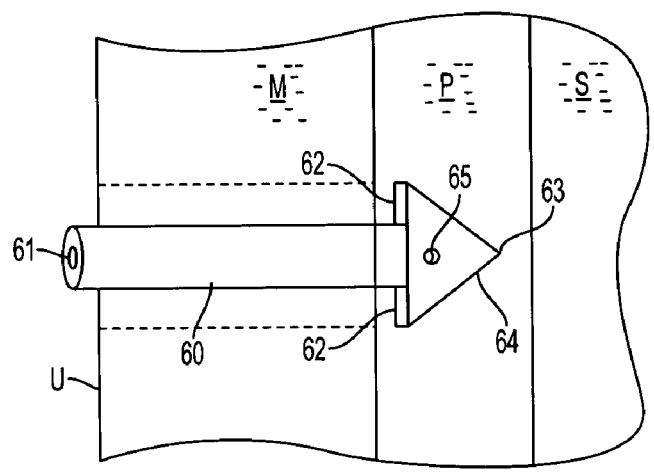
FIG. 6A
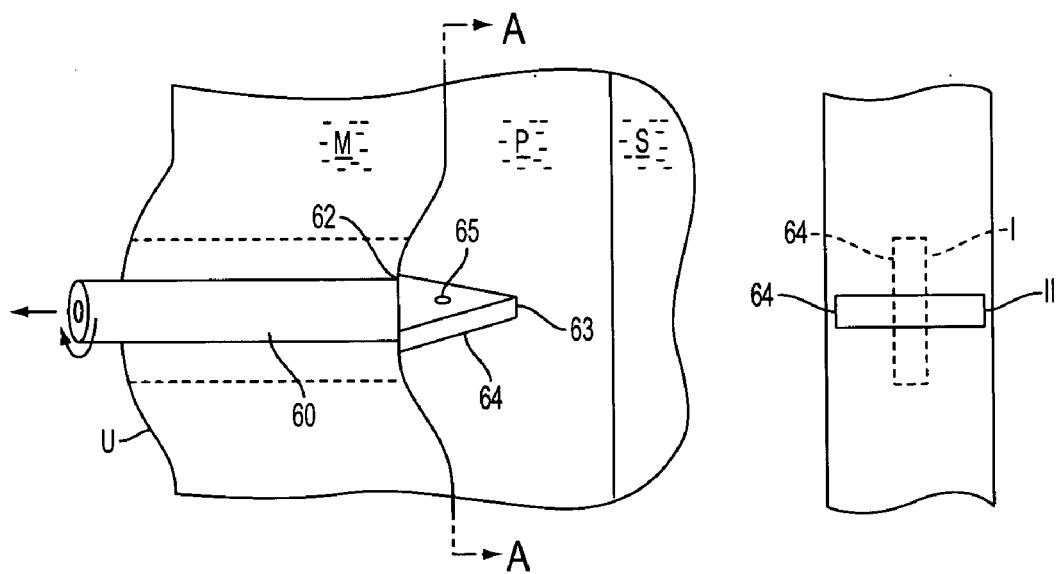
FIG. 6B
FIG. 6C

APPARATUS AND METHODS FOR TREATING FEMALE URINARY INCONTINENCE

REFERENCE TO RELATED APPLICATION

The present application is a continuation-in-part of U.S. patent application Ser. No. 09/678,500, filed Oct. 2, 2000 now U.S. Pat. No. 6,470,219.

FIELD OF THE INVENTION

This invention relates to apparatus and methods for treating urinary incontinence, and more particularly, for treating female urinary incontinence in humans by injecting a bulking material into a space formed between the mucosal and submucosal layers of the urethral wall to cause localized reduction of the urethral cross-sectional flow area.

BACKGROUND OF THE INVENTION

The term "urinary incontinence" refers to involuntary leakage of urine from the body in an uncontrolled manner. One cause of incontinence is increased mobility of the bladder outlet, referred to as "bladder outlet hypermobility," whereby the bladder and proximal urethra do not maintain their normal anatomic positions during transient periods of increased bladder pressure. In addition, there is a small region of circular muscle surrounding the middle portion of the urethra in the female called the "urethral sphincter," which also participates in the controlled release of urine from the bladder. If the bladder outlet becomes too mobile and/or if the urinary sphincter or any other part of the urinary system malfunctions, the result may be urinary incontinence.

Urinary incontinence can generally be characterized into two types, one of which is called "stress incontinence" and the other "urge incontinence." Stress incontinence refers to involuntary loss of urine during coughing, laughing, sneezing, jogging or other physical activity that causes a sufficient increase in intra-abdominal pressure. Urge incontinence refers to the involuntary loss of urine due to unwanted bladder contraction that may be associated with an almost uncontrollable desire to urinate. "Mixed incontinence" refers to a combination of both urge and stress incontinence.

Heretofore, many different types of treatment have been utilized to treat female urinary incontinence including surgical and non-surgical procedures including the precisely-controlled injection, i.e., under cystoscopic visualization, of collagen or other material into the tissue surrounding or adjacent to the bladder outlet. In addition, drug therapy also has been utilized, for example, drugs to treat the detrusor muscle, which is the bladder wall muscle responsible for contracting and emptying the bladder. All of these procedures and therapies have drawbacks, are relatively expensive and, in the case of injections, require the equipment and training necessary to perform cystoscopic visualization of the urethra and bladder outlet. There is therefore a need for a new and improved apparatus and method for treatment of female urinary incontinence.

In view of the drawbacks of previously-known devices, it would be desirable to provide apparatus and methods for treating female urinary incontinence by injecting a bulking agent into a "potential space," defined herein as the space that can be formed at the interface between the mucosal and submucosal layers of the urethral wall and/or bladder outlet, so that the bulking agent effectively induces localized narrowing of the urethral lumen and/or bladder outlet.

It further would be desirable to provide apparatus and methods for treating female urinary incontinence that allow a physician to inject a bulking agent into the potential space without the need for a cystoscopic visualization device, e.g., a cystoscope.

It still further would be desirable to provide apparatus and methods for treating female urinary incontinence by techniques that do not require external surgical incisions and do not result in external scarring.

SUMMARY OF THE INVENTION

In view of the foregoing, it is an object of the present invention to provide apparatus and methods for treating female urinary incontinence by injecting a bulking agent into the "potential space" at the interface between the mucosal and submucosal layers of the urethral wall and/or bladder outlet, so that the bulking agent locally narrows the urethral lumen and/or bladder outlet.

It further is an object of the present invention to provide apparatus and methods for treating female urinary incontinence that allow a physician to inject a bulking agent into the potential space without the need for a visualization device.

It still further is an object of the present invention to provide apparatus and methods for treating female urinary incontinence by techniques that do not require external surgical incisions and do not result in external scarring.

These and other objects of the present invention are accomplished by providing a remodeling device comprising a handle, an elongated shaft having a distal region including an expandable member, and an injection needle.

In a preferred embodiment, the handle is coupled to a proximal end of the elongated shaft and is manipulated by the physician to insert the distal region into a patient's urethra, either individually or using an appropriate introducer sheath. The handle includes an actuator for expanding the expandable member, and at least one port for delivering a bulking material to the injection needle.

In accordance with one aspect of the present invention, the expandable member is affixed to the elongated shaft in the distal region, near a distal end of the elongated shaft. The expandable member may comprise a balloon or mechanically actuated basket, and is configured to be moved between a contracted position, which permits insertion of the expandable member through the urethra and into the patient's bladder, and a deployed position, wherein the expandable member anchors against the bladder outlet. The expandable member facilitates tactile positioning of the injection needle at desired treatment sites within the urethra, without the need for direct visualization.

In accordance with another aspect of the present invention, a means for forming a localized inward protrusion of the urethral wall preferably is used in conjunction with the apparatus of the present invention. The means for forming preferably comprises a diametrally stepped portion within the distal region of the elongated shaft. In one embodiment, the stepped portion comprises an enlarged diameter proximal portion disposed proximally adjacent to a smaller diameter distal portion, to which the expandable member may be affixed.

The insertion of the enlarged proximal portion into the urethra causes the urethral wall to expand and conform to the shape of the enlarged proximal portion, while the step in diameters between the enlarged proximal portion and smaller diameter distal portion causes a localized portion of the urethral wall to protrude inwardly. In particular, the urethral wall protrudes inwardly to cause a localized narrowing of the urethral lumen in the vicinity of the smaller diameter distal portion as a result of the step in diameter.

In a preferred embodiment, a proximal surface of the expandable member may cooperate with the means for forming so that the portion of the urethral wall protruding into the urethral lumen forms an annulus. The means for forming optionally may comprise suction ports disposed in the vicinity of the stepped region to enhance the degree to which the urethral wall tissue is drawn towards the center of the urethral lumen.

The injection needle is disposed within the elongated shaft in the vicinity of the stepped region, and is movable between retracted and deployed positions. In the retracted position, the needle is disposed within the elongated shaft, while in the deployed position, the needle penetrates into the inwardly protruding annulus of the urethral wall. The injection needle includes a tip and at least one delivery port disposed in a lateral surface of the needle, through which a bulking agent may be delivered into a space formed at the interface of the mucosal and submucosal layers within the inwardly protruding annulus of the urethral wall.

When deployed, the injection needle extends into the potential space at the mucosal/submucosal interface, so that bulking agent may be delivered into the potential space. The bulking material causes a localized narrowing of the urethral lumen, thereby alleviating symptoms associated with urinary incontinence.

In alternative embodiments of the present invention, the needle may assume a straight or curved shape when extended to the deployed position. In another embodiment, the needle comprises a shape-memory material that curves inwardly in a helical fashion after piercing the mucosa. In yet a further alternative embodiment, the needle include barbs on its tip, so that once the tip penetrates the mucosal layer, it may be retracted to partially expand the potential space prior to injection of the bulking agent.

Methods of using the apparatus of the present invention to induce localized narrowing of the urethral lumen, and to reduce or eliminate the effects of urinary incontinence, also are provided.

BRIEF DESCRIPTION OF THE DRAWINGS

Further features of the invention, its nature and various advantages will be more apparent from the accompanying drawings and the following detailed description of the preferred embodiments, in which:

FIG. 3 is a side view of the device of FIG. 1 deployed prior to injection of a bulking agent;

FIG. 4 is a side view of the device of FIG. 3 during the injection a bulking agent;

FIG. 5 is a side view of an alternative embodiment of the present invention comprising a curved needle tip;

FIGS. 6A-6C are, respectively, a first and second side view of a further alternative remodeling device of the present invention and a cross-sectional schematic of the patient's tissue with the device deployed.

DETAILED DESCRIPTION OF THE INVENTION

The apparatus and methods of the present invention are directed to a remodeling device for delivering a bulking agent at the interface between the mucosal and submucosal layers of the urethral wall, without direct visualization of the needle used to deliver the bulking agent. In accordance with one aspect of the present invention, means are provided for forming a localized inward protrusion of the urethral wall to cause a localized narrowing of the urethral lumen and facilitate delivery of the bulking agent at the mucosal/submucosal layer interface.

Figure 1:
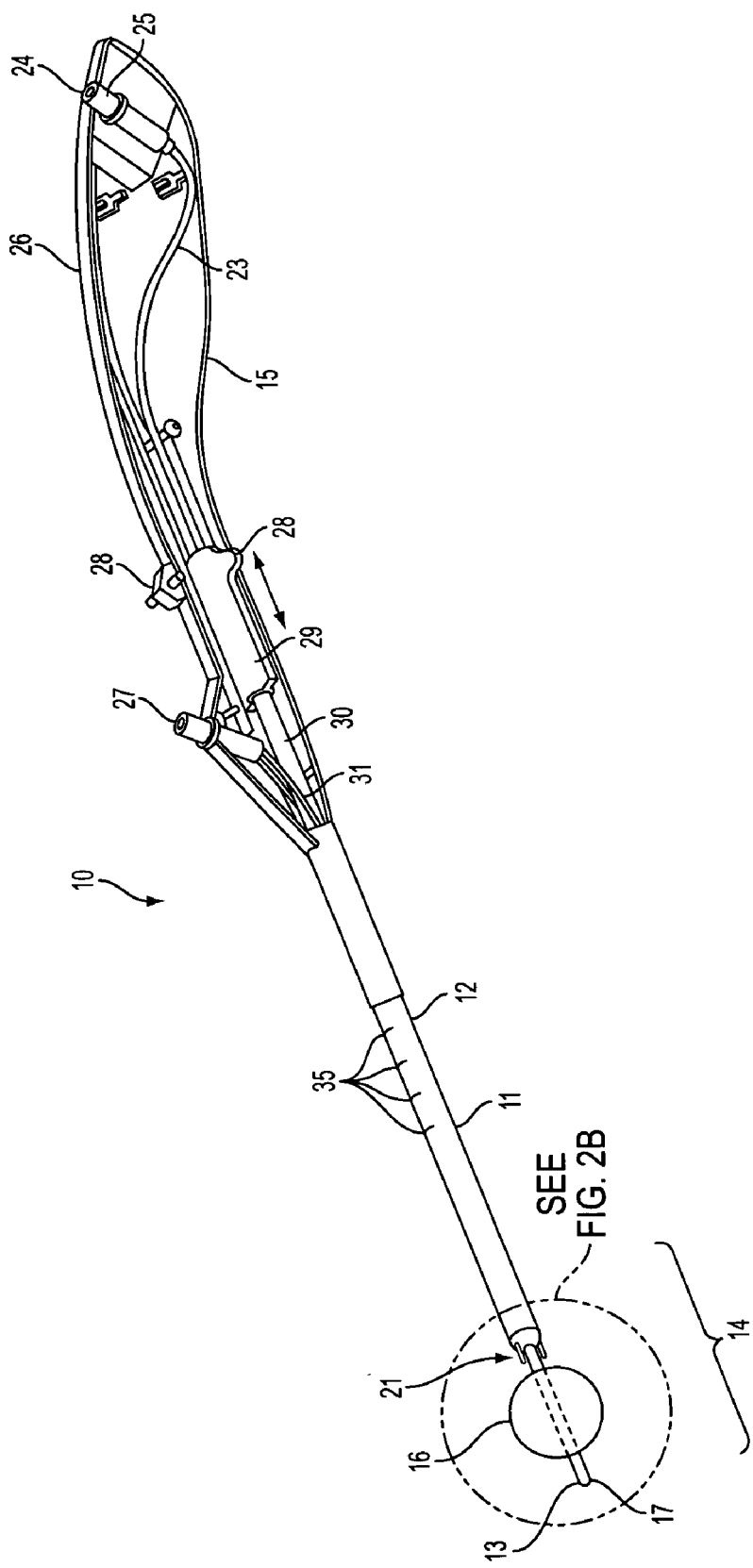
FIG. 1 provides a side view of a distal section and a side sectional view of a proximal section of a first remodeling device constructed in accordance with principles of the present invention.

Referring to FIG. 1, an illustrative embodiment of remodeling device 10 of the present invention comprises elongated shaft 11 having proximal end 12, distal end 13 and distal region 14. Proximal end 12 is coupled to handle 15, while distal region 14 includes expandable member 16 and atraumatic tip 17 on distal end 13. Distal region 14 preferably includes a diametral step formed where enlarged diameter proximal portion 18 meets smaller diameter distal portion 19. Preferably, transition 20 between the larger and smaller diameter portions is radiused, as more clearly depicted in FIGS. 2A and 2B. Remodeling device 10 further includes at least one needle 21 for delivering a bulking agent into the tissue that protrudes into the annular space between the proximal surface of expandable member 16 and transition 20, as described more fully hereinafter.

In one embodiment, expandable member 16 comprises balloon 22 formed from a compliant or semi-compliant material, such as polyurethane, latex, polyethylene or isoprene. In accordance with one aspect of the present invention, balloon 22 is inflated via inflation tube 23 that extends from inflation port 24 of handle 15, and through elongated shaft 11 to the interior of balloon 22. Inflation port 24 preferably also includes valve 25 that maintains balloon 22 in an inflated state when the balloon is inflated with a suitable fluid or gas. As described hereinafter, expandable member 16 advantageously may be used to position distal region 14 of elongated shaft 11 within a female patient's urethra using tactile sense, rather than direct visualization.

Handle 15 includes housing 26, which is configured to be grasped by a human hand, injection port 27 that is coupled to needles 21, and actuator 28, which is selectively actuated by the physician to extend needles 21 from, or retract needles 21 into, elongated shaft 11. Needles 21 are coupled via rod 30 to slide block 29 affixed to actuator 28, and are in fluid communication with injection port 27 via tubing 31. Proximal and distal movement of actuator 28 causes translational motion of slide block 29 and rod 30 (indicated by arrows in FIG. 1), which in turn translates needles 21.

Needles 21 are affixed in block 32 disposed within elongated shaft 11 and connected to rod 30, so that reciprocation of actuator 28 causes deployment or retraction of needles 21. Each needle 21 includes a distal end having tissue-penetrating tip 33 and delivery port 34 (see FIG. 2B), a proximal end coupled to tubing 31, and a lumen extending therebetween. Delivery port 34 preferably is disposed in a lateral surface of needle 21. Needles 21 preferably comprise stainless steel or a shape-memory alloy.

In accordance with the principles of the present invention, there preferably is a step in diameters between enlarged proximal portion 18 and smaller diameter distal portion 19 that causes a portion of the urethral wall to protrude inwardly to cause a localized narrowing of the urethral lumen when the elongated shaft is inserted into the urethra. Applicants have observed that introduction of a shaft having approximately the same or a slightly larger diameter than a typical diameter of a human female urethra will cause the tissue adjacent to transition 20 to protrude inwardly into the urethral lumen and cause a localized narrowing of the urethral lumen. Applicants' invention employs this effect to facilitate location of the interface between the mucosal and submucosal layers of the urethral wall, as described hereinafter. Remodeling device 10 further includes measurement indicia 35 disposed on the exterior of elongated shaft 11 to assist in initial placement of the device in the patient's urethra.

Referring now to FIG. 3, a method of using the apparatus of the present invention for treating female urinary incontinence is described. The apparatus of the present invention may be used in conjunction with an introducer and introducer sheath assembly to facilitate insertion of the device into a patient's urethra or, alternatively, may be inserted individually without the use of the introducer and sheath assembly. When the introducer and introducer sheath are used, the introducer is loaded into the introducer sheath and both are covered with a lubricant jelly. The assembly then is introduced into urethra U of the patient so that the tip of the introducer passes transurethrally into the patient's bladder. Once this has been accomplished, the introducer is removed, leaving the introducer sheath in place with its distal extremity extending into the bladder.

Distal region 14 and elongated shaft 11 of remodeling device 10 then is covered with a lubricant jelly. Distal end 13 of remodeling device 10 is carefully introduced into the introducer sheath and advanced into the sheath for a predetermined distance, e.g., as determined by measurement indicia 35. Typically, because of the known length of 2-½ to 4 cm of urethra U before bladder B, the device is introduced for a distance of approximately 6 cm to ensure that expandable member 16 is positioned within the patient's bladder B. Thereafter, the introducer sheath is retracted so that it is completely out of bladder B, but so that it still is surrounding elongated shaft 11.

Once expandable member 16 is positioned in a contracted state within bladder B, the expandable member is deployed by insufflating a suitable gas or fluid, e.g., water, through inflation port 24. Expandable member 16 then is retracted and anchored against bladder outlet O, so that deployed needle tip 33 is disposed at a predetermined distance distal of bladder outlet O. It should be understood by those skilled in the art of anatomy that a location "distal of the bladder outlet" refers to a direction toward the proximal end of elongated shaft 11 because the urethral lumen is located distal of the bladder outlet.

In a preferred embodiment, the step in diameters between enlarged proximal portion 18 and smaller distal portion 19 causes urethra U to expand and conform to the shape of distal region 14. In particular, a localized portion of the urethral wall has been observed to protrude inwardly into the urethral lumen to cause a localized narrowing of the urethral lumen. More specifically, the urethral wall tissue protrudes into the annulus defined by transition 20, smaller diameter distal portion 19 and the proximal surface of expandable member 16, as depicted in FIG. 3.

After locating the elongated shaft within the urethra by the above-described method, actuator 28 on handle 15 is actuated to deployed needles 21, so that needle tips 33 puncture mucosa M of urethra U. Preferably, needles 21 exit through transition 20 at an angle between 5-60 degrees with respect to longitudinal axis A of elongated shaft 11. More preferably, a relatively low angle is employed so that delivery port 34 of needle 21 does not immediately pass through potential space P at the interface between mucosal M and submucosal S layers, but rather is disposed substantially at the interface, which defines potential space P.

Referring to FIG. 4, injection of a bulking agent into potential space P is described. After needle 21 is deployed, as described with respect to FIG. 3, bulking agent 40 is delivered via injection port 24, tubing 23, the lumen of needle 21, and delivery port 34. Bulking agent 40 preferably is deposited into potential space P within the localized inward protrusion of the urethral wall, so that bulking agent 40 spreads along the interface between the mucosal and submucosal layers and substantially encircles a region of potential space P distal of bladder outlet O. Applicant has observed that the interface between the mucosal and submucosal layers may be readily separated, and that delivery of the bulking agent at this interface causes localized narrowing of the urethral lumen.

Alternatively, the step in diameters between enlarged proximal portion 18 and smaller distal portion 19 may be omitted so that elongated shaft 11 does not cause a localized inward protrusion of the urethral wall prior to injecting the bulking agent. When the means for forming the localized inward protrusion is not used, it is expected that bulking agent injected into the submusoca ultimately will be directed back towards the urethral wall because the resistance provided by the submucosa is greater than that provided by the potential space. Accordingly, even without using the means for forming, it is expected that the bulking agent will impose a resistance upon the urethral wall to cause a localized narrowing of the urethral lumen.

After injection of the bulking agent, actuator 28 is moved proximally to retract needles 21, expandable member 16 is contracted, and remodeling device 10 and the introducer sheath are withdrawn from the urethra. In accordance with principles of the present invention, bulking agent 40, which may comprise a synthetic material, collagen or a collagen-based material, biocompatibly-coated carbon microspheres or other materials, retains its shape within potential space P and narrows the urethral lumen, thereby reducing or eliminating symptoms associated with urinary incontinence.

Referring now to FIG. 5, an alternative embodiment of the present invention is described wherein needles 21' are curved in the deployed state and transition 20' further includes suction ports 50. Elements of the embodiment of FIG. 5 are described with like-primed numbers used in the description of the embodiment of FIGS. 1 and 2, and is otherwise as described above with respect to FIGS. 1 and 2, except that handle 15 and elongated shaft 11 further include tubing for communicating suction to suction ports 50.

Needle 21' has tip 33' including blunt end 52, and preferably comprises a shape-memory material, e.g., Nitinol, that self-deploys to the curved configuration shown in FIG. 5. Needles 21' are configured so that when deployed, the tips of the needles pierce mucosal layer M and are deflected inwardly when they contact the substantially stiffer submucosal layer S. Blunt end 52 serves to separate the mucosal layer from the submucosal layer along the interface, thereby facilitating delivery of bulking agent 40 into potential space P.

Use and operation of the embodiment of FIG. 5 is similar to that described above with respect to FIGS. 3 and 4. In particular, elongated shaft 11' is advanced into a patient's urethra U with needle 21' in a retracted position within the confines of the elongated shaft. Expandable member 16' is positioned within bladder B, as described hereinabove, and the expandable member is deployed and then retracted against bladder outlet O.

Suction then may be drawn through suction ports 50, if provided, to enhance the extent to which the urethral wall protrudes into the urethral lumen adjacent to distal region 14' to cause a localized narrowing of the urethral lumen.

Needle 21' then is actuated, for example, by distally advancing the actuator, so that needle tip 33' initially pierces through mucosa M at approximately a 90-degree angle. After piercing through mucosa M, and when needle tip 33 is still within potential space P, the shape-memory properties of the needle cause tip 33 to curve inward toward mucosa M. Needle tip 33 is configured not to pierce back through mucosa M because blunt end 52 mitigates the force imposed by needle tip 33 upon mucosa M.

The portion of needle 21' that is proximal of needle tip 33 is biased outwardly so that it stretches and separates the mucosa from the submucosa, thereby creating potential space P and facilitating delivery of the bulking agent. Moreover, because a longer length of the needle may be deployed in the potential space, there is an increased likelihood that the needle tip and delivery port will be disposed within the potential space, as opposed to the surrounding tissue.

The bulking agent then may be delivered into potential space P via delivery ports 34' of needles 21'. Confirmation that the bulking agent is being delivered into the potential space, rather than the urethral lumen, can be obtained by continuing to draw suction through suction ports 50 and monitoring that bulking agent is not aspirated through the suction ports. In accordance with methods described hereinabove with respect to FIGS. 3 and 4, the bulking agent preferably is delivered into potential space P distal of bladder outlet O so that it disperses to substantially encircle a region of potential space P near the bladder outlet. After delivery of the bulking agent, needles 21' are retracted, expandable member 16' is contracted, and the remodeling device is removed from the patient's urethra.

Referring now to FIGS. 6A-6C, a further alternative needle embodiment suitable for use with the apparatus and methods of the present invention is described. In FIG. 6A, needle 60 has proximal and distal ends, lumen 61 extending therebetween, and barbs 62 disposed proximally of tip 63. As illustratively depicted in FIG. 6A, tip 63 and barbs 62 form arrow-shaped head 64.

Needle 60 further comprises at least one delivery port 65 disposed in a lateral surface of head 64. Delivery port 65 is in fluid communication with lumen 61, which in turn is in fluid communication with the injection port on the handle, as described hereinabove with respect to the embodiment of FIGS. 1-3.

Operation of this embodiment is as follows. Once the elongated shaft is located within the urethra using the expandable member, needles 60 are advanced by actuation of the handle so that needle heads 64 pierce mucosa M, as shown by the dashed lines in FIG. 6A, until needle head 64 is advanced to the interface of the mucosal and submucosal layers, i.e., to potential space P.

Once head 64 is advanced through mucosa M and disposed within potential space P, a noticeable change in resistance may be experienced by the physician, because greater resistance is encountered when the head contacts the substantially stiffer mucosa.

Once needle head 64 is situated within potential space P, needle 60 is rotated approximately ninety degrees, as shown in FIG. 6B, so that head 64 is aligned at an angle with respect to the path along which the needle head was advanced through mucosa M. This may be accomplished, for example, by rotating the proximal end of needle 60, or alternatively by a mechanism that rotates needle 60 at the conclusion of its translation.

FIG. 6C provides a cross-sectional view along line A-A of FIG. 6B at the junction between mucosa M and potential space P. In FIG. 6C, position I depicts an entrance path by which needle head 64 pierces mucosa M and enters potential space P, while position II is an approximately orthogonal to position I.

After needle 60 is inserted and rotated, it is retracted proximally against the wall of mucosa M when in position II, so that barbs 62 engage mucosa M and increase the local area within potential space P, as depicted in FIG. 6B. A bulking agent then may be injected via delivery port 65 to fill the locally-expanded section of potential space P. Upon completion of delivery of the bulking agent, needle head 64 is rotated back to position I and then proximally retracted via the original path formed within mucosa M. The needle then is retracted within the elongated shaft, the expandable member is contracted, and the remodeling device is removed from the patient's urethra.

Figure 7A:
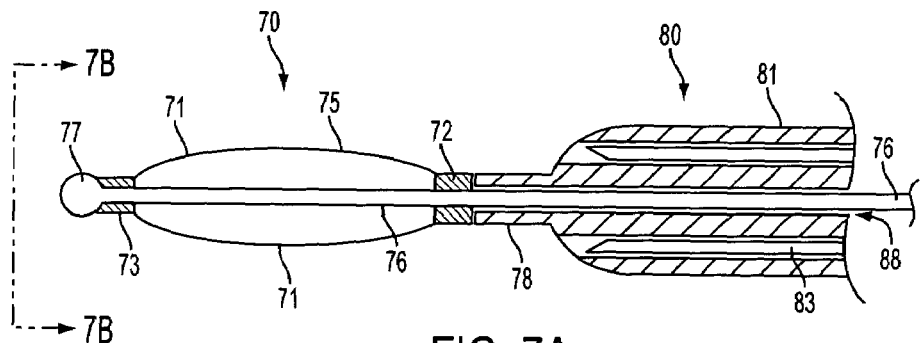
FIGS. 7A-7D are side and cross-sectional views of an alternative embodiment of an expandable member suitable for use in the remodeling device of the present invention.
Figure 7B:
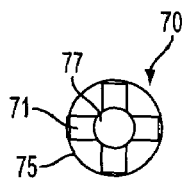
Figure 7C:
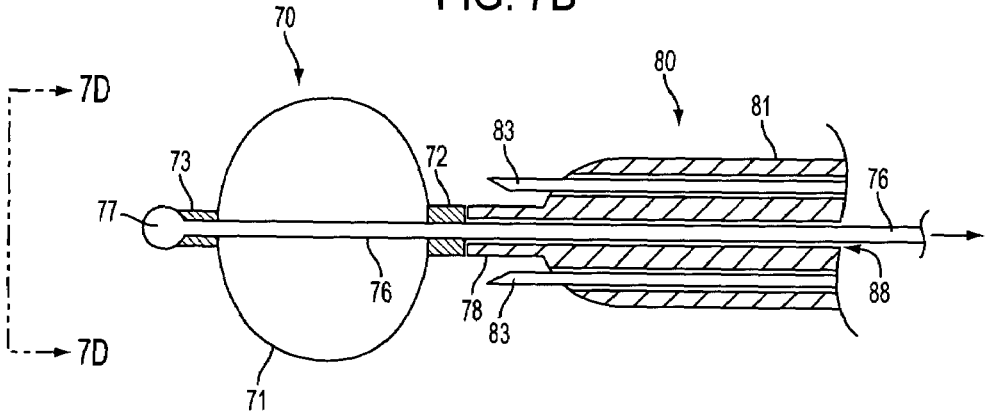
Figure 7D:
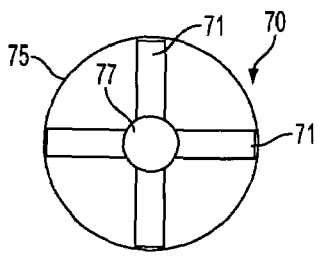

Referring now to FIGS. 7A-7D, the distal end of an alternative embodiment of the remodeling device of FIG. 1 is described. In FIG. 7A, balloon 22 has been replaced by mechanically expandable basket 70. Basket 70 comprises a plurality of flexible struts 71 joined at either end to rings 72 and 73. Struts 71, which preferably are covered by biocompatible elastomeric membrane 75, are biased to a contracted position, illustrated in FIGS. 7A and 7B, but bow outwardly to assume a deployed position when compressively loaded, as illustrated in FIGS. 7C and 7D.

Rod 76 is slidably disposed through lumen 88 of elongated shaft 81 and includes atraumatic distal stop 77 and a proximal end disposed in the handle of the remodeling device. The proximal end of rod 76 is configured to be retracted proximally, so that when the rod is retracted, struts 71 are compressively loaded. Rod 76 further is disposed through a lumen in rings 72 and 73, as shown in FIG. 7A. Rings 72 and 73 may be permitted to float on rod 76. Alternatively, ring 72 may be affixed to distal stop 77, ring 73 may be affixed to the distal end of elongated shaft 78, or both rings may be so fixed.

In operation, remodeling device 80 is inserted into the patient's urethra in the manner described hereinabove for the embodiment of FIGS. 1-3. Once basket 70 is positioned within the bladder, the proximal end of rod 76 is retracted proximally by a physician to deploy mechanically expandable basket 70. More particularly, as rod 76 is retracted, ring 72 abuts the distal end of elongated shaft 81, while distal stop 77 abuts against ring 73 and pulls ring 73 proximally, thereby causing struts 71 to bow outwardly. Elastomeric membrane 75 conforms to the expanded shape of struts 71 in the deployed configuration.

Once deployed, needles 83 are deployed from elongated shaft 81 to penetrate the urethral wall to deliver a bulking agent to the mucosal/submucosal interface. After delivery of the bulking agent is completed, basket 70 may be returned to the contracted configuration, depicted in FIGS. 7A and 7B, by advancing rod 76 distally to remove the compressive load from struts 71, thereby permitting struts 71 and elastomeric membrane 75 to return to the contracted position shown in FIGS. 7A and 7B.

Figure 2:
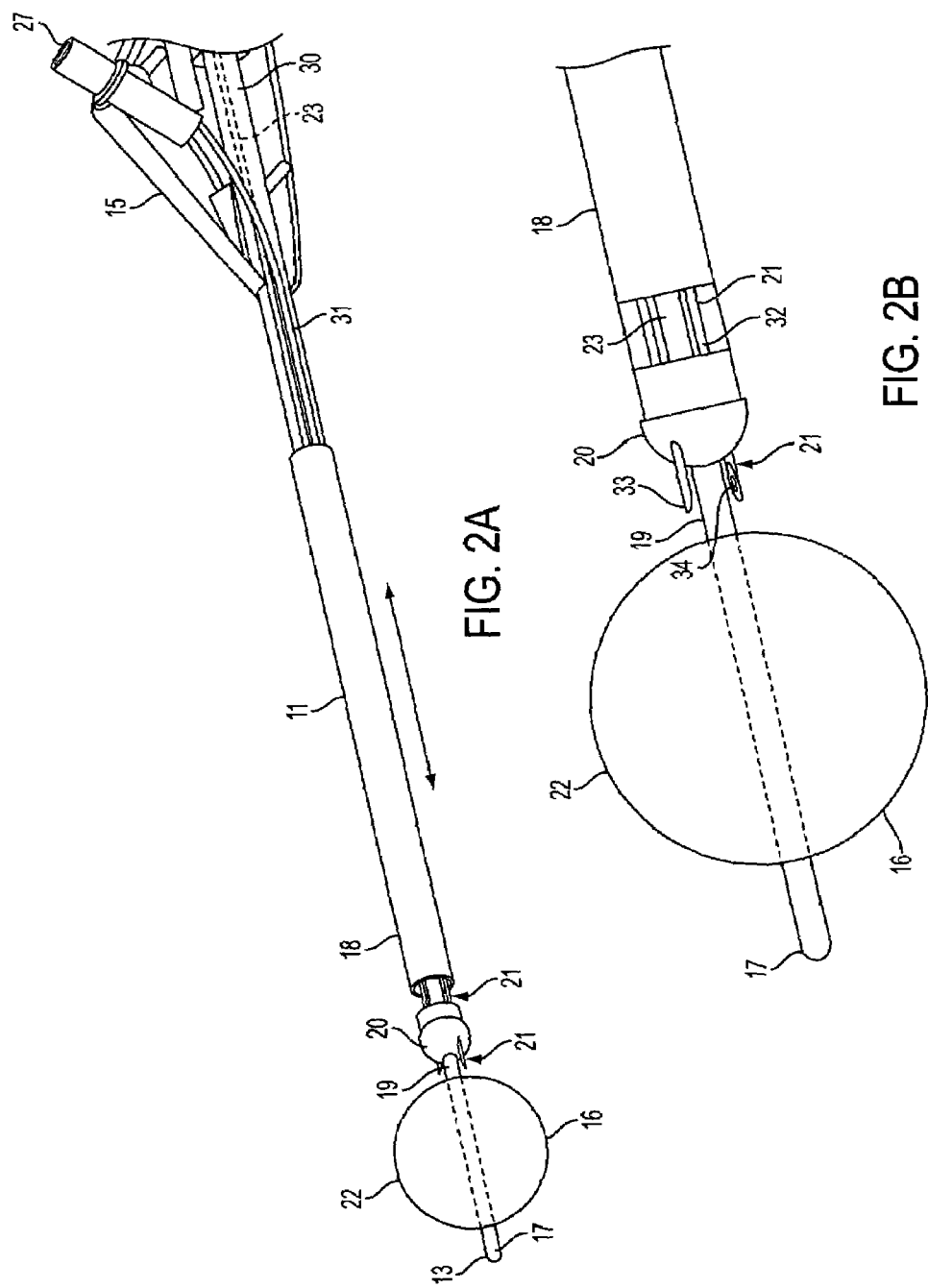
FIGS. 2A-2B are side sectional views of the distal section of the device of FIG. 1.

It is to be understood that arrangements other than the stepped diameters illustrated in FIGS. 1-3 may be employed to accomplish the feature of having the urethral wall protrude inwardly into the urethral lumen to cause a localized narrowing of the urethral lumen. For example, instead of enlarged diameter proximal portion, the means for forming a localized protrusion of the urethral wall may comprise distal region 14 of elongated shaft 11 that includes an expandable cuff that may be selectively enlarged to urge the urethral wall tissue to protrude inwardly. In this case, the elongated shaft may include an outer layer formed from an elastomer, e.g., polyurethane or latex, that may be selectively expanded when fluid is introduced into selected regions within the shaft. In view of the teachings provided hereinabove, further alternative configurations will be apparent to those of skill in the art of medical device design.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. Apparatus for remodeling a treatment site within the urinary tract of a female patient, the urinary tract including a urethra having a urethral lumen and a bladder having a bladder outlet, the apparatus comprising:
   an elongated shaft having a proximal end, a distal end and a distal region disposed adjacent to the distal end; a handle coupled to the proximal end;
   an expandable member affixed to the distal region in the vicinity of the distal end, the expandable member adapted to be deployed in the bladder and anchored against the bladder outlet;
   means for selectively forming a localized inward protrusion of the urethral wall; and
   a needle disposed to penetrate the urethral wall in the vicinity of the localized inward protrusion to inject a bulking agent at the interface of the mucosal and submucosal layers.

2. The apparatus of claim 1 wherein the means for forming comprises a diametrally stepped portion of the distal region.

3. The apparatus of claim 2 wherein the diametrally stepped portion comprises an enlarged diameter proximal portion and a smaller diameter distal portion.

4. The apparatus of claim 1 wherein the means for forming further comprises a suction port.

5. The apparatus of claim 1 wherein the means for forming further comprises a barb disposed on a distal end of the needle.

6. The apparatus of claim 1 wherein a distal portion of the needle is curved in the deployed position.

7. The apparatus of claim 1 wherein the needle comprises a shape-memory material.

8. The apparatus of claim 1 wherein the needle includes an injection port disposed in a lateral surface of the needle.

9. The apparatus of claim 1 wherein the expandable member comprises a balloon.

10. The apparatus of claim 1 further comprising a rod slidably disposed in a lumen of the elongated shaft, wherein the expandable member comprises an expandable basket coupled to the rod, so that proximal retraction of the rod with respect to the elongated shaft causes the expandable basket to deploy.

11. The apparatus of claim 1 wherein the proximal end of the elongated shaft further comprises a plurality of indicia suitable for use in positioning the distal region within the urethra.

12. A method for remodeling a treatment site within the urinary tract of a female patient, the urinary tract including a urethra having a urethral lumen and a bladder having a bladder outlet, the method comprising:
   providing apparatus comprising a handle and an elongated shaft coupled to the handle, the elongated shaft having a distal region and a needle, the distal region comprising an expandable member;
   inserting the elongated shaft into the urethra until the expandable member is positioned within the bladder;
   locating the needle at a position within the urethra;
   deploying the expandable member within the bladder;
   retracting the handle proximally to seat the expandable member against the bladder outlet;
   moving the needle to penetrate the urethral wall;
   injecting a bulking agent at an interface between the mucosal and submucosal layers of the urethral wall to cause localized narrowing of the urethral lumen; and
   forming a localized inward protrusion of the urethral wall prior to injecting the bulking agent.

13. The method of claim 12 wherein forming a localized inward protrusion of the urethral wall comprises applying suction to a portion of the urethral wall via a suction port disposed in the distal region of the elongated shaft.

14. The method of claim 13 further comprising monitoring the output of the suction port to determine whether bulking agent is being delivered within the urethral lumen.

15. The method of claim 12 wherein the needle further comprises a distal tip having a barb, and moving the needle to penetrate tissue in the vicinity of the localized inward protrusion of the urethral wall facilitates separation at the interface between the mucosal layer from the submucosal layer.

16. The method of claim 12 wherein deploying the expandable member comprises inflating a balloon.

* * * * *